(12) United States Patent
Cho et al.

(10) Patent No.: US 10,874,301 B2
(45) Date of Patent: Dec. 29, 2020

(54) RAMAN SIGNAL MEASURING METHOD AND APPARATUS, AND BIOMETRIC INFORMATION ANALYZING APPARATUS INCLUDING THE RAMAN SIGNAL MEASURING APPARATUS

(71) Applicants: SAMSUNG ELECTRONICS CO., LTD., Suwon-si (KR); MASSACHUSETTS INSTITUTE OF TECHNOLOGY, Cambridge, MA (US)

(72) Inventors: Seongho Cho, Gwacheon-si (KR); Gajendra Singh, Cambridge, MA (US); Juneyoung Lee, Seongnam-si (KR)

(73) Assignees: SAMSUNG ELECTRONICS CO., LTD., Suwon-si (KR); MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 1073 days.

(21) Appl. No.: 15/353,198

(22) Filed: Nov. 16, 2016

(65) Prior Publication Data
US 2017/0135582 A1 May 18, 2017

(30) Foreign Application Priority Data

Nov. 17, 2015 (KR) .......................... 10-2015-0161054

(51) Int. Cl.
*G01J 3/44* (2006.01)
*A61B 5/00* (2006.01)
(Continued)

(52) U.S. Cl.
CPC ............ *A61B 5/0075* (2013.01); *A61B 5/725* (2013.01); *G01J 3/027* (2013.01); *G01J 3/0232* (2013.01);
(Continued)

(58) Field of Classification Search
CPC ............... G01N 21/65; G01N 21/658; G01N 2021/656; G01J 3/44; G01J 3/02
(Continued)

(56) References Cited

U.S. PATENT DOCUMENTS 5,946,090 A    8/1999  Tashiro et al.
2006/0188869 A1*  8/2006  Zeskind ............ G01N 15/1475
                                                           435/4
(Continued)

FOREIGN PATENT DOCUMENTS

JP      10-148573 A      6/1998
KR  10-2011-0133778 A   12/2001
(Continued)

OTHER PUBLICATIONS

P. Matousek et al., "Efficient Rejection of Fluorescence from Raman Spectra Using Picosecond Kerr Gating", Applied Spectroscopy, Society for Applied Spectroscopy, vol. 53, No. 12, 1999, pp. 1485-1489, XP-000903126.
(Continued)

*Primary Examiner* — Md M Rahman
(74) *Attorney, Agent, or Firm* — Sughrue Mion, PLLC

(57) ABSTRACT

Provided are a Raman signal measuring method and apparatus which use a difference in a time scale between Raman scattered light and fluorescence. Thus, after exciting light is incident upon a target object, light scattered from the target object may be detected before the target object generates fluorescence in response to the exciting light. As a result, a Raman signal in which background fluorescence is reduced may be obtained.

27 Claims, 12 Drawing Sheets

(51) Int. Cl.
*G01J 3/36* (2006.01)
*G01J 3/10* (2006.01)
*G01J 3/02* (2006.01)
*G01J 3/18* (2006.01)
*G01J 3/28* (2006.01)
*G01J 3/14* (2006.01)
*G01N 21/65* (2006.01)
*G01J 3/12* (2006.01)

(52) U.S. Cl.
CPC . *G01J 3/10* (2013.01); *G01J 3/14* (2013.01); *G01J 3/18* (2013.01); *G01J 3/2803* (2013.01); *G01J 3/36* (2013.01); *G01J 3/44* (2013.01); *G01N 21/65* (2013.01); *G01J 2003/1217* (2013.01); *G01J 2003/1234* (2013.01); *G01J 2003/2806* (2013.01); *G01J 2003/4424* (2013.01); *G01N 2201/068* (2013.01); *G01N 2201/0697* (2013.01); *G01N 2201/06113* (2013.01); *G01N 2201/12* (2013.01)

(58) Field of Classification Search
USPC ........................................................ 356/301
See application file for complete search history.

(56) References Cited

U.S. PATENT DOCUMENTS

| | | |
|---|---|---|
| 2007/0060806 A1 | 3/2007 | Hunter et al. |
| 2007/0222982 A1 | 9/2007 | Tuschel et al. |
| 2012/0212812 A1* | 8/2012 | Weber ................. G03B 21/604 359/454 |
| 2014/0113283 A1 | 4/2014 | Suh et al. |
| 2014/0226158 A1* | 8/2014 | Trainer ................. G01J 3/0218 356/336 |
| 2016/0202178 A1* | 7/2016 | Acosta ...................... G01J 3/18 356/303 |
| 2018/0280723 A1* | 10/2018 | Enwemeka .......... A61N 5/0616 |
| 2019/0374092 A1* | 12/2019 | Wu ........................... A61B 1/07 |

FOREIGN PATENT DOCUMENTS

| | | |
|---|---|---|
| KR | 10-2012-0132668 A | 12/2012 |
| WO | 2014/125171 A1 | 8/2014 |

OTHER PUBLICATIONS

Communication dated Apr. 20, 2017, from the European Patent Office in counterpart European Application No. 16198556.9.

* cited by examiner

RAMAN SIGNAL MEASURING METHOD AND APPARATUS, AND BIOMETRIC INFORMATION ANALYZING APPARATUS INCLUDING THE RAMAN SIGNAL MEASURING APPARATUS

CROSS-REFERENCE TO RELATED APPLICATION

This application claims priority from Korean Patent Application No. 10-2015-0161054, filed on Nov. 17, 2015, in the Korean Intellectual Property Office, the disclosure of which is incorporated herein in its entirety by reference.

BACKGROUND

1. Field

The present disclosure relates to a Raman signal measuring method and apparatus, and a biometric information analyzing apparatus including the Raman signal measuring apparatus.

2. Description of the Related Art

Raman spectroscopy may be used for analyzing the composition of various materials by emitting exciting light toward a target object and measuring inelastic scattering from the object that is generated by the exciting light.

If light is incident on a sample to be analyzed, inelastically scattered light having a wavelength different from that of the incident light may be detected. This frequency shift between incident light and scattered light is called "Raman shift" and indicates the state of vibrational or rotational energy of molecules. It is known that the intensity of Raman scattered light directly corresponds to the concentration of molecules, and thus molecular analysis using Raman spectroscopy may be usefully used for molecular analysis.

The intensity of Raman scattered light signals is very low, resulting in difficulties in performing Raman spectroscopy. Thus, optical systems for amplifying Raman scattered light signals have been proposed.

In addition, samples to be analyzed may absorb incident light as well as scattering the incident light, and may thus exhibit strong fluorescence, resulting in additional difficulties in performing Raman spectroscopy. This fluorescence is called "background fluorescence," and devices such as filters are used to separate Raman signals from background fluorescence. However, the use of devices such as filters may distort Raman signals having relatively low degrees of intensity and may have a negative effect on the precision of Raman signals.

SUMMARY

Provided are a Raman signal measuring method and apparatus that are less affected by background fluorescence, and a biometric information analyzing apparatus including the Raman signal measuring apparatus.

Additional aspects will be set forth in part in the description which follows and, in part, will be apparent from the description, or may be learned by practice of the presented exemplary embodiments.

According to an aspect of an exemplary embodiment, a Raman signal measuring method includes: emitting exciting light from an optical illumination system including a light source toward an target object to be analyzed; and detecting light scattered from the target object, by using an optical detection system including an optical detector, before fluorescence is generated from the target object by the exciting light.

The Raman signal measuring method may further include: transmitting a first timing signal to the optical illumination system; and transmitting a second timing signal to the optical detection system, wherein a transmission time difference between the first and second timing signals may be shorter than a time period taken for the fluorescence to be generated from the target object by the exciting light.

The emitting of the exciting light from the light source to the target object may be started according to the first timing signal, and the detecting of the light scattered from the target object may be terminated according to the second timing signal.

The light scattered from the target object may be blocked from being incident on the optical detector according to the second timing signal.

The emitting of the exciting light may include emitting pulsed light.

The pulsed light may have a pulse width shorter than a time period taken for the fluorescence to be generated from the target object by the exciting light.

The optical detector may have a light detection response time shorter than a time period taken for the fluorescence to be generated from the target object by the exciting light.

According to an aspect of another exemplary embodiment, a Raman signal measuring apparatus includes: an optical illumination system including a light source configured to emit exciting light to a target object to be analyzed; an optical detection system configured to detect light scattered from the target object according to wavelengths of the scattered light, the optical detection system including a light splitting element and an optical detector; and a timing controller configured to control operation timing of the optical illumination system and the optical detection system.

The timing controller may be configured to transmit a timing signal so as to terminate detection of light by the detection optical system before fluorescence is generated from the target object by the exciting light emitted from the light source.

The timing controller may be further configured to transmit a first timing signal to the optical illumination system so as to allow the exciting light of the light source to reach the target object, and transmit a second timing signal to the detection optical system so as to stop the optical detection system from detecting light scattered from the target object.

The optical illumination system may be configured to emit pulsed light to the target object.

The optical illumination system may include a continuous laser and a chopper.

The optical illumination system may include a pulse laser.

The pulse light may have a pulse width shorter than a time difference between the first and second timing signals.

The optical detector may have a light detection response time shorter than a time difference between the first and second timing signals.

The light source may emit exciting light to the target object according to the first timing signal.

The optical illumination system may further include a first shutter configured to open or close an optical path of light emitted from the light source toward the target object, and the first shutter may be opened according to the first timing signal.

The optical detection system may further include a second shutter configured to open or close an optical path along which light scattered from the target object may be incident on the optical detector, and the second shutter may be closed according to the second timing signal.

The light splitting element may include a beam splitting device configured to divide light scattered from the target object according to wavelengths of the scattered light.

The beam splitting device may include a prism.

The beam splitting device may include a grating device.

The light splitting element may include a linear variable filter having different wavelength pass bands according to positions where light is incident on the linear variable filter.

The light splitting element may include a plurality of dichroic filters.

The dichroic filters may include: a first dichroic filter configured to facilitate propagation of light in a first wavelength band and reflect the light in other wavelength bands; and a second dichroic filter arranged in an optical path of the light reflected from the first dichroic filter so as to facilitate propagation of the light in a second wavelength band and reflect the light in other wavelength bands.

A plurality of band pass filters having different wavelength pass bands may be arranged between the optical detector and the dichroic filters.

The light splitting element may include a plurality of band pass filters having different wavelength pass bands.

According to an aspect of another exemplary embodiment, a biometric information analyzing apparatus includes: an optical illumination system including a light source configured to emit excitant light to a target object to be analyzed; an optical detection system including an optical detector configured to detect light scattered from the target object; a timing controller configured to control operation timing of the optical illumination system and the optical detection system; and a signal processor configured to analyze properties of the target object using a signal output from the optical detection system.

BRIEF DESCRIPTION OF THE DRAWINGS

These and/or other aspects will become apparent and more readily appreciated from the following description of exemplary embodiments, taken in conjunction with the accompanying drawings in which.

DETAILED DESCRIPTION

Figure 1:
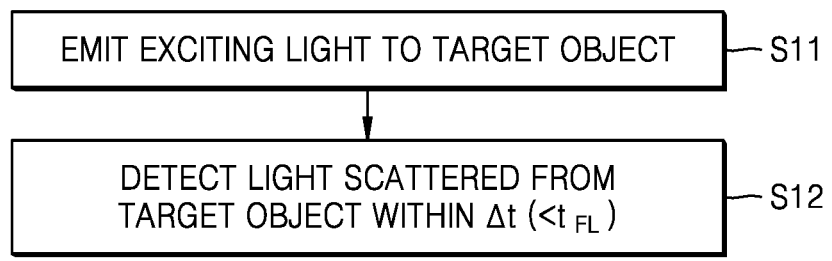
FIG. 1 is a flowchart illustrating a Raman signal measuring method according to an exemplary embodiment.

Exemplary embodiments will now be described with reference to the accompanying drawings. In the drawings, like reference numbers refer to like elements, and also the size of each element may be exaggerated for clarity of illustration. The exemplary embodiments described herein are for illustrative purposes only, and various modifications may be made therefrom.

In the following description, when an element is referred to as being "above" or "on" another element, it may be directly on the other element while making contact with the other element or may be above the other element without making contact with the other element.

It will be understood that although the terms "first", "second", etc. may be used herein to describe various elements, these elements should not be limited by these terms. These terms are only used to distinguish one element from another.

As used herein, the singular forms "a," "an" and "the" are intended to include the plural forms as well, unless the context clearly indicates otherwise. It will be further understood that the terms "comprises" and/or "comprising" used herein specify the presence of stated features or elements, but do not preclude the presence or addition of one or more other features or elements.

In the present disclosure, terms such as unit or module are used to denote a unit having at least one function or operation and implemented with hardware, software, or a combination of hardware and software.

FIG. 1 is a flowchart illustrating a Raman signal measuring method according to an exemplary embodiment.

Exciting light (also referred to herein as "excitant light") is emitted toward a target object to be analyzed, so as to obtain a Raman signal (operation S11).

The Raman signal is light inelastically scattered from molecules of a target object while being shifted in wavelength when exciting light is emitted toward the target object. Light shifted to have a wavelength longer than its original wavelength is called "Stokes-shifted Raman signal," and light shifted to have a wavelength shorter than its original wavelength is called "anti-Stokes Raman signal." The degree of frequency shift is unique to each molecule species. Therefore, information about molecules of the target object may be obtained from the Raman signal.

Light emerging from the target object to which the exciting light is emitted includes various kinds of light in addition to the Raman signal. For example, molecules of the target object may absorb the exciting light and may thus transit to an excited state. Then, the molecules may return to a ground state and may emit light in an amount that corresponds to the energy difference between the excited state and the ground state. In this case, while the molecules transit from the excited state to the ground state, the molecules may emit light of various wavelengths according to paths between the excited state and the ground state. Light emitted as described above has wavelengths which are longer than the wavelength of incident light and overlap much of the wavelength band of the Raman signal and also has a high signal level. Therefore, it is difficult to separate the Raman signal from light emerging from the target object.

According to the Raman signal measuring method of the exemplary embodiment, light scattered from the target object is detected before the generation of fluorescence from the target object (operation S12). That is, scattered light is detected within $\Delta t$ ($<t_{FL}$) where $t_{FL}$ refers to a time period until the generation of fluorescence.

Figure 2:
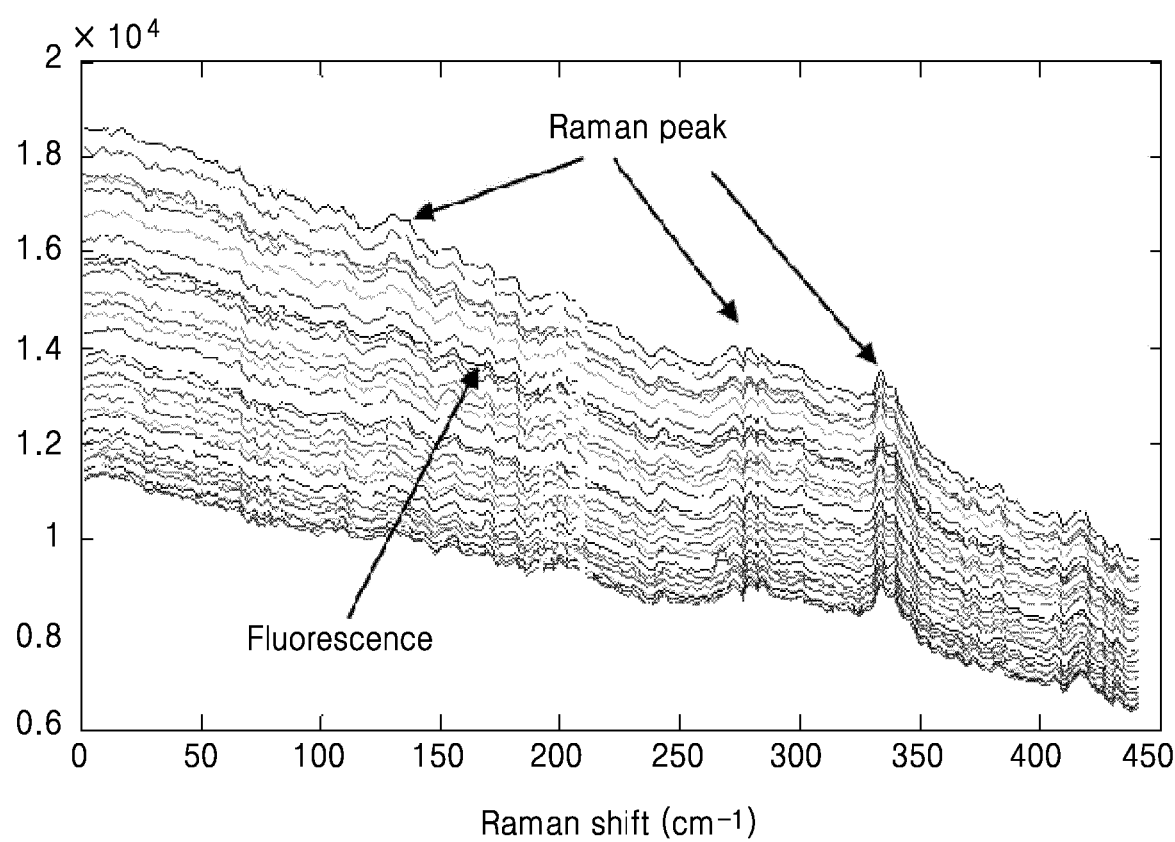
FIG. 2 illustrates exemplary spectrums of light emerging from a target object to be analyzed.

FIG. 2 is a graph illustrating exemplary spectrums of light emerging from a target object to be analyzed.

In the graph, the horizontal axis refers to the reciprocal of the wavelength of the emerging light, that is, the wavenumber of the emerging light, and the vertical axis refers to the intensity of the emerging light. The number of curves in the graph indicates the number of measurements, and the curves are arranged from the lower side in chronological order.

Referring to the graph, Raman peaks shown at particular wavelength shift positions correspond to a Raman signal, and the remainder is background fluorescence. As shown in the graph, since the signal level of the background fluorescence is very high, it is difficult to extract the Raman peaks, and thus additional optical elements may be used to separate the Raman signal.

According to the Raman signal measuring method of the exemplary embodiment, in addition to a Raman signal, fluorescence generated in response to exciting light is analyzed to find the principle and time scale of fluorescence generation and thus to directly obtain the Raman signal while reducing the influence of such background fluorescence.

Figure 3:
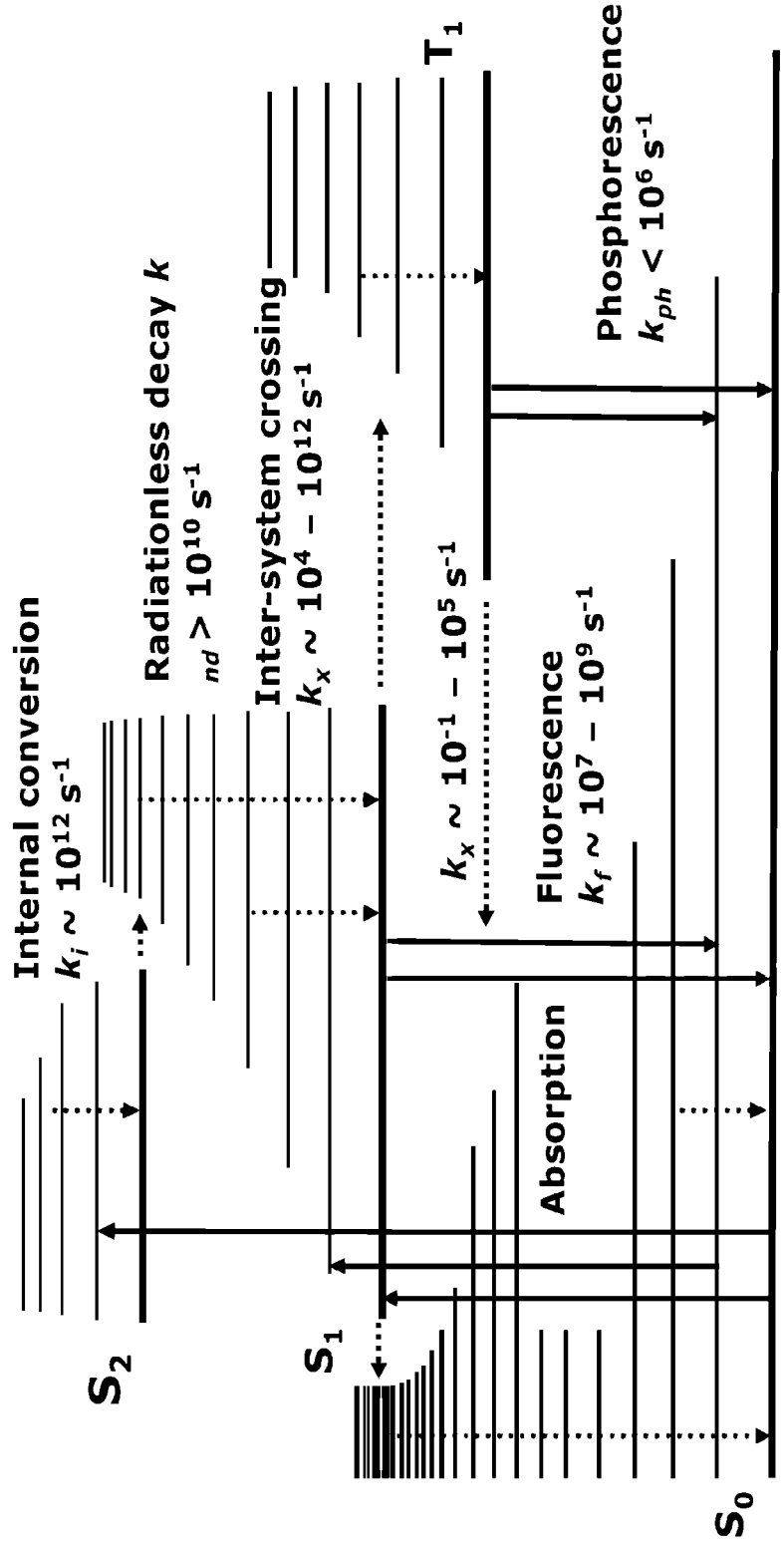
FIG. 3 is a Jablonski diagram for explaining why fluorescence is included in a general Raman spectrum.

FIG. 3 is a Jablonski diagram for explaining why fluorescence is included in a general Raman spectrum.

The Jablonski diagram is an energy diagram showing the life history of electrons excited by the absorption of light.

Referring to FIG. 3, molecules having excited electrons emit energy through internal conversion and also through radiationless decay caused by collision with surrounding molecules. The molecules do not transit to a ground state by collision with surrounding molecules, but instead remain in a certain excited state and spontaneously emit light. This light is fluorescence. That is, if exciting light is emitted to a target object to be analyzed, the target object emits fluorescence after a time period for internal conversion, radiationless decay, and spontaneous emission.

After internal conversion and radiationless decay, some of the molecules that remain in the excited state may transit to the ground state through a singlet-triplet (inter-system crossing) transition, and thus may emit light more slowly. This light is phosphorescence.

It takes about several nanoseconds until fluorescence is emitted, and microseconds until phosphorescence is emitted.

It is known that it takes about several femtoseconds until Raman light emerges. Therefore, after exciting light is emitted toward the target object, if the detection of an optical signal from the target object is completed before fluorescence is generated from the target object, for example, within about one nanosecond to about two nanoseconds, the optical signal may be a Raman signal substantially not affected by fluorescence.

Figure 4:
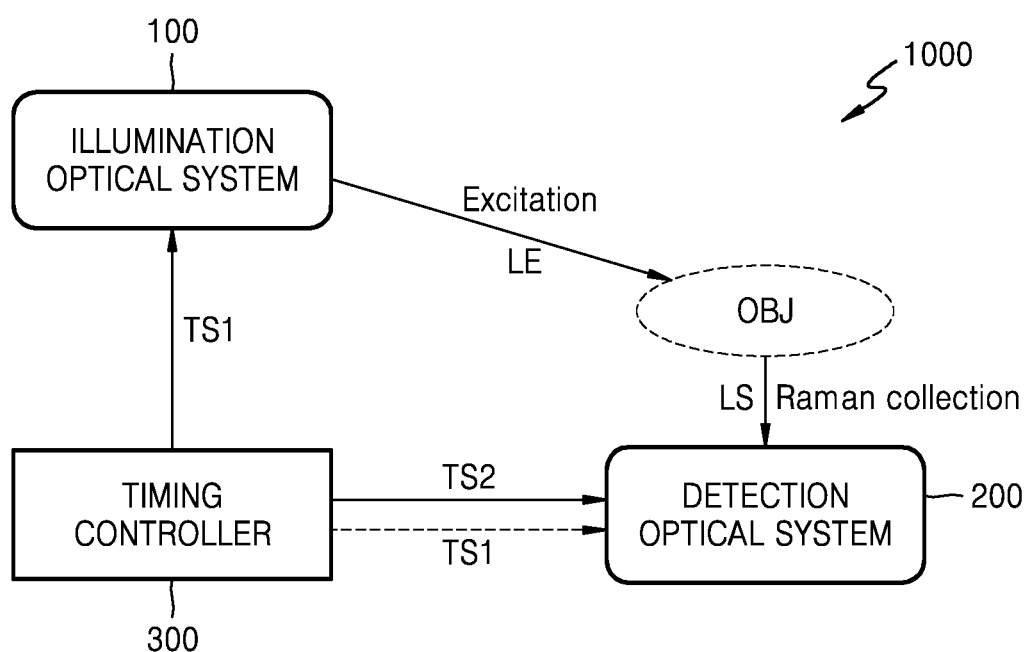
FIG. 4 is a schematic view illustrating a Raman signal measuring apparatus according to an exemplary embodiment.

FIG. 4 is a schematic view illustrating a Raman signal measuring apparatus 1000 according to an exemplary embodiment.

The Raman signal measuring apparatus 1000 includes: an illumination optical system (also referred to herein as an "optical illumination system") 100 including a light source configured to emit exciting light LE to a target object OBJ; a detection optical system (also referred to herein as an "optical detection system") 200 including a light splitting element and an optical detector so as to detect light LS scattered from the target object OBJ according to the wavelength of the scattered light LS; and a timing controller 300 configured to control operation timing of the illumination optical system 100 and the detection optical system 200.

The target object OBJ is an object whose composition will be analyzed by Raman spectroscopy. For example, the target object OBJ may be a living body, such as a human body, or a food. For example, the target object OBJ may be a human body from which substances such as glucoses, keratin, squalene, ceramides, or collagen will be measured. In addition, the target object OBJ may be a food whose freshness will be measured or may be a sample for analyzing air or water pollution.

The illumination optical system 100 includes the light source configured to emit exciting light LE. According to properties of the target object OBJ to be analyzed, the light source may emit light having a wavelength band suitable for analyzing the properties. For example, the light source may be configured to emit near infrared light having a wavelength band of about 800 nm to about 2500 nm. For example, the light source may include a device such as a light emitting diode (LED) or a laser diode (LD). The illumination optical system 100 may further include at least one optical element that directs light emitted from the light source toward the target object OBJ, for example, guiding light emitted from the light source to an intended position of the target object OBJ.

Exciting light LE emitted from the illumination optical system 100 to the target object OBJ is scattered by various molecules included in the target object OBJ, and some of the scattered light is Raman shifted light. The Raman-shifted light includes vibrational spectroscopic information unique to each molecule species.

The detection optical system 200 detects light LS scattered from the target object OBJ when exciting light LE is emitted to the target object OBJ. The scattered light LS includes light of which wavelengths are shifted, to different degrees, from the wavelength of the exciting light LE. Therefore, the detection optical system 200 includes the light splitting element and the optical detector so as to detect the scattered light LS according to the wavelengths thereof.

Light emerging from the target object OBJ may include a significant amount of fluorescence in addition to Raman scattered light LS, and thus the Raman signal measuring apparatus 1000 of the exemplary embodiment includes the timing controller 300 so as to detect an optical signal that does not include such fluorescence by controlling the detection optical system 200.

In order to detect light emerging from the target object OBJ before the generation of fluorescence, the illumination optical system 100 and the detection optical system 200 may enter a lock-in state under the control of the timing controller 300.

The timing controller 300 may include a local oscillator capable of generating waves in a gigahertz (GHz) or higher frequency band, so as to generate a proper timing signal.

The timing controller 300 may generate a timing signal so as to terminate the detection of light by the detection optical system 200 before fluorescence is generated from the target object OBJ in response to exciting light LE emitted from the illumination optical system 100 to the target object OBJ. The timing controller 300 may transmit a first timing signal TS1 to the illumination optical system 100, and the illumination optical system 100 may emit exciting light LE to the target object OBJ according to the first timing signal TS1. At the same time, the timing controller 300 may transmit the first timing signal TS1 to the detection optical system 200. Then, the detection optical system 200 may detect light LS scattered from the target object OBJ according to the first timing signal TS1 received from the timing controller 300. However, this is an example. It is optional whether the timing controller 300 transmits the first timing signal TS1 to the detection optical system 200. When the illumination optical system 100 does not emit exciting light LE to the target object OBJ, since light is not scattered from the target object OBJ, the detection optical system 200 may wait in a detection mode, and if exciting light LE is emitted to the target object OBJ according to the first timing signal TS1, the detection optical system 200 may detect light LS scattered from the target object OBJ.

The timing controller 300 may transmit a second timing signal TS2 to the detection optical system 200. After the first timing signal TS1 is transmitted, the second timing signal TS2 is transmitted to the detection optical system 200 before the elapse of a time period $t_{FL}$ required until fluorescence is generated from the target object OBJ in response to exciting light LE. That is, a time difference $\Delta t$ between the second timing signal TS2 and the first timing signal TS1 is shorter than the time period $t_{FL}$ taken for the target object OBJ to generate fluorescence. The detection of light by the detection optical system 200 may be terminated according to the second timing signal TS2.

The optical detector of the detection optical system 200 has a light detection response time shorter than the time difference $\Delta t$. In other words, the light detection response time of the optical detector is shorter than the time period $t_{FL}$ taken for the target object OBJ to generate fluorescence. If the light detection time of the optical detector is longer than the time period $t_{FL}$, a Raman signal may not be detected before the generation of fluorescence. Therefore, the optical detector may include a material allowing for high-speed sensing within a light detection response time of several nanoseconds.

Figure 5:
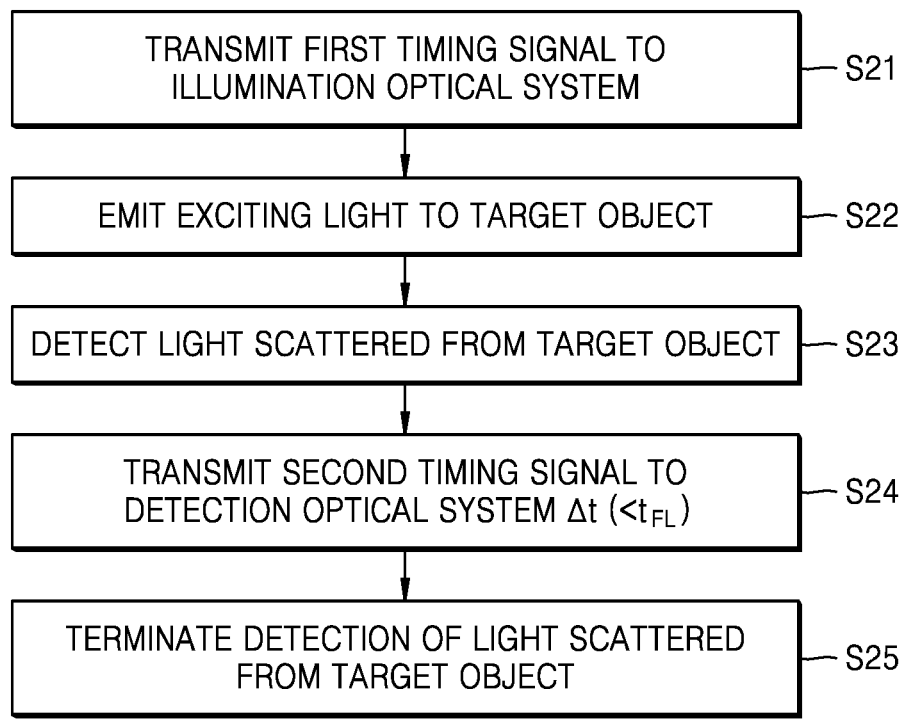
FIG. 5 is a flowchart illustrating a Raman signal measuring method according to another exemplary embodiment.

FIG. 5 is a flowchart illustrating a Raman signal measuring method according to another exemplary embodiment.

First, a first timing signal is transmitted to an illumination optical system (operation S21).

The illumination optical system emits exciting light LE to a target object OBJ according to the first timing signal (operation S22), and a detection optical system detects light scattered from the target object OBJ (operation S23).

Next, a second timing signal is transmitted to the detection optical system (operation S24). A time difference $\Delta t$ between the second timing signal and the first timing signal is shorter than a time period $t_{FL}$ for the target object OBJ to generate fluorescence.

The detection of light scattered from the target object is terminated according to the second timing signal (operation S25).

Figure 6:
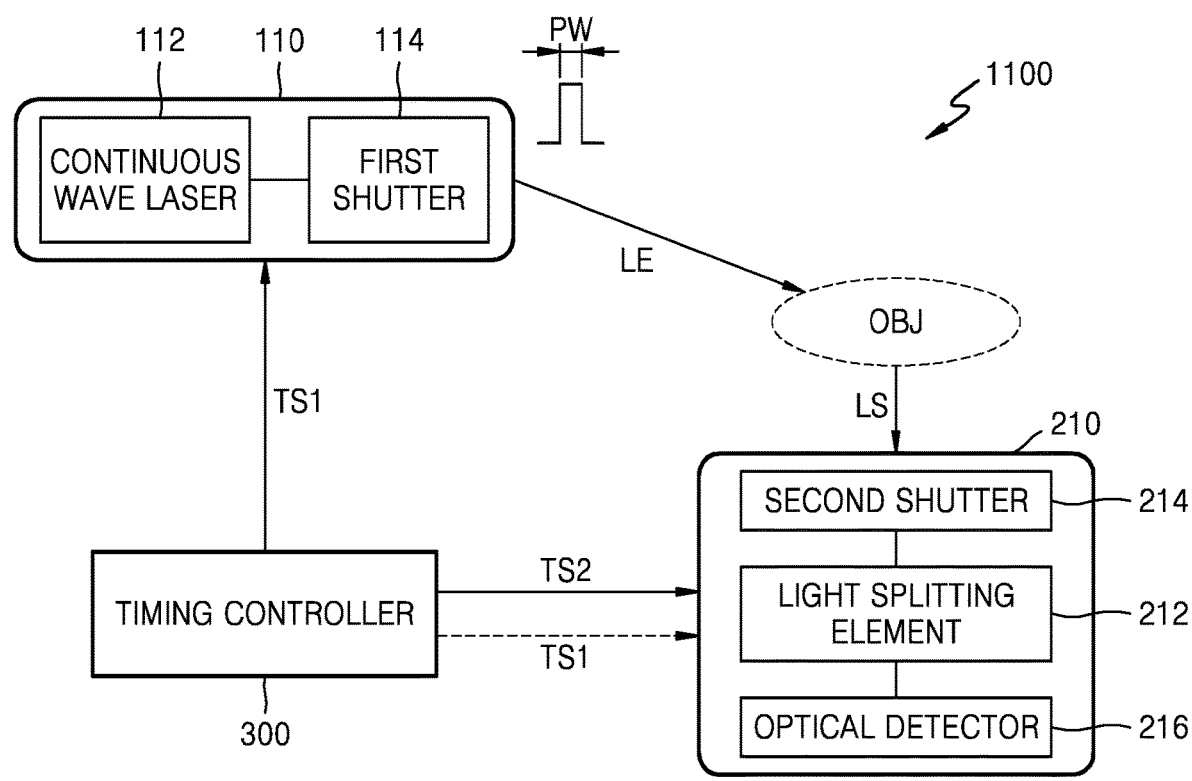
FIG. 6 is a schematic view illustrating a Raman signal measuring apparatus according to another exemplary embodiment.

FIG. 6 is a schematic view illustrating a Raman signal measuring apparatus 1100 according to another exemplary embodiment.

The Raman signal measuring apparatus 1100 includes an illumination optical system (also referred to herein as an "optical illumination system") 110, a detection optical system (also referred to herein as an "optical detection system") 210, and a timing controller 300.

The illumination optical system 110 may emit pulsed light. To this end, the illumination optical system 110 may include a continuous wave laser 112 and a first shutter 114.

The first shutter 114 may block light emitted from the continuous wave laser 112 such that the light may not reach a target object OBJ, and if a first timing signal TS1 is transmitted from the timing controller 300, the first shutter 114 may be opened to allow light emitted from the continuous wave laser 112 to reach the target object OBJ. The first shutter 114 may be a chopper configured to convert light emitted from the continuous wave laser 112 into pulsed light before the light is incident on the target object OBJ. For example, the first shutter 114 may be controlled so that the first shutter 114 may stay in a light transmission mode for a predetermined time period and return to a light blocking mode, and this switching between the light transmission mode and the light blocking mode may be carried out in a mechanical or electronic manner. The first shutter 114 may be controlled to stay in the light blocking mode so as to prevent light emitted from the continuous wave laser 112 from reaching the target object OBJ, and if a first timing signal TS1 is transmitted from the timing controller 300, the first shutter 114 may be controlled to be in the light transmission mode for a predetermined time period so as to allow light emitted from the continuous wave laser 112 to reach the target object OBJ. The predetermined time period may determine a pulse width PW. The pulse width PW may be shorter than a time period $t_{FL}$ for the target object OBJ to generate fluorescence after exciting light LE is incident on the target object OBJ. For example, the pulse width PW may be several nanoseconds or shorter. For example, the pulse width PW may be about one nanosecond to about two nanoseconds.

The detection optical system 210 may include a second shutter 214, a light splitting element 212, and an optical detector 216.

If the timing controller 300 transmits a first timing signal TS1 to the detection optical system 210, the second shutter 214 may be opened according to the first timing signal TS1, and the optical detector 216 may detect light LS scattered from the target object OBJ. However, this is optional. If exciting light LE is not incident on the target object OBJ, since light is not scattered from the target object OBJ, the detection optical system 210 may wait in a detection mode. For example, when the second shutter 214 is opened, if exciting light LE is emitted from the illumination optical system 110 to the target object OBJ according to the first timing signal TS1, light LS scattered from the target object OBJ may be detected.

The timing controller 300 transmits a second timing signal TS2 to the detection optical system 210. A time difference $\Delta t$ between the second timing signal TS2 and the first timing signal TS1 is shorter than a time period $t_{FL}$ for the target object OBJ to generate fluorescence in response to exciting light LE. If the second shutter 214 is closed according to the second timing signal TS2, light emerging from the target object OBJ is not incident on the optical detector 216. That is, the detection of light by the detection optical system 210 is terminated according to the second timing signal TS2. The second shutter 214 is illustrated as being disposed between the light splitting element 212 and the target object OBJ. However, this is an exemplary arrangement. For example, the second shutter 214 may be disposed between the light splitting element 212 and the optical detector 216.

As described above, the optical detector 216 may have a light detection response time shorter than the time difference $\Delta t$. If the light detection time of the optical detector 216 is longer than the time difference $\Delta t$, a Raman signal may not be detected before the generation of fluorescence. Therefore, the optical detector 216 may have a high-speed sensing ability within a light detection response time of about several nanoseconds.

Figure 7:
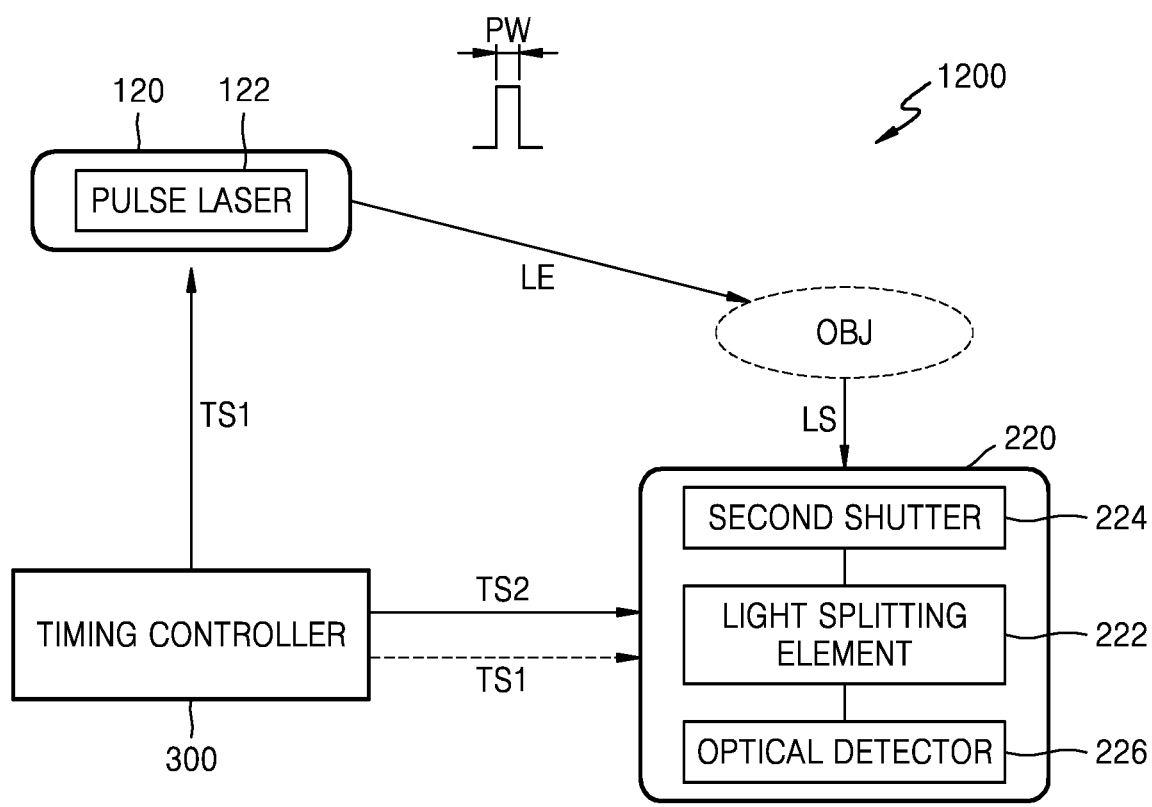
FIG. 7 is a schematic view illustrating a Raman signal measuring apparatus according to another exemplary embodiment.

FIG. 7 is a schematic view illustrating a Raman signal measuring apparatus 1200 according to another exemplary embodiment.

The Raman signal measuring apparatus 1200 includes an illumination optical system 120, a detection optical system 220, and a timing controller 300.

In the current exemplary embodiment, the illumination optical system 120 of the Raman signal measuring apparatus 1200 includes a pulse laser 122 as a light source. The pulse laser 122 may be a mode-locking pulse laser. Since the mode-locking pulse laser generates light by phase-matched multimode lasing, the mode-locked pulse laser may be used to generate very-high-frequency, high-power pulses. The pulse laser 122 may have a pulse width PW shorter than a time period $t_{FL}$ for a target object OBJ to generate fluorescence in response to exciting light LE. Alternatively, the pulse laser 122 may have a pulse width PW shorter than a time difference Δt between first and second timing signals TS1 and TS2.

The detection optical system 220 may include a second shutter 224, a light splitting element 222, and an optical detector 226, and the optical detector 226 may have a light detection response time shorter than the time period $t_{FL}$ for the target object OBJ to generate fluorescence in response to exciting light LE. Alternatively, the optical detector 226 may have a light detection response time shorter than the time difference Δt between first and second timing signals TS1 and TS2. Alternatively, the optical detector 226 may have a light detection response time shorter than the pulse width PW of light emitted from the pulse laser 122.

Figure 8:
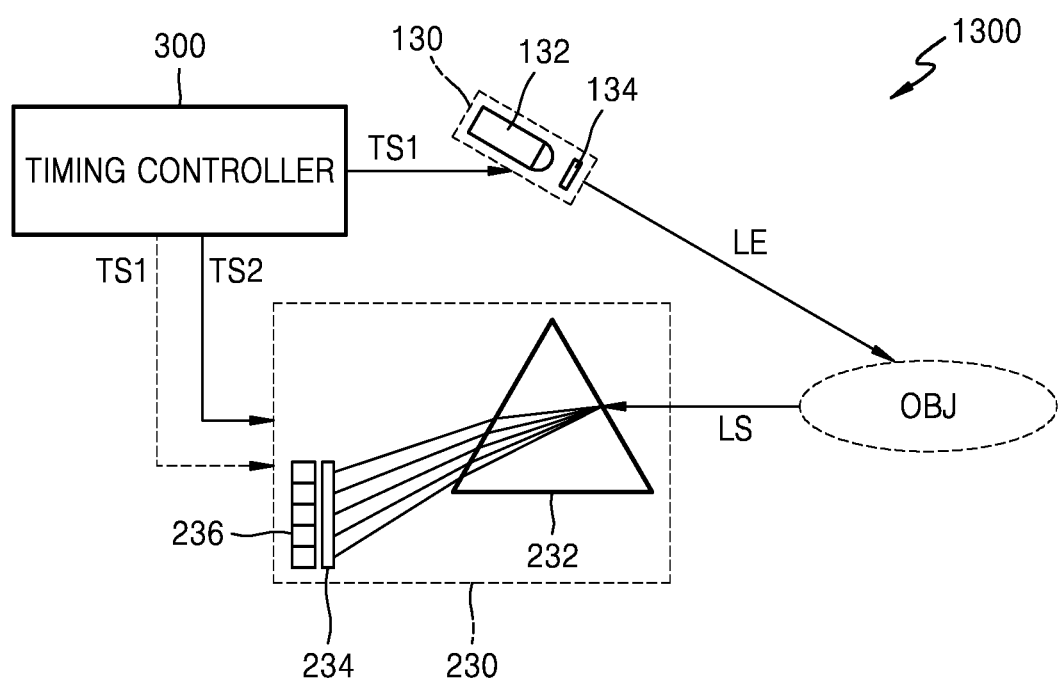
FIG. 8 is a schematic view illustrating a Raman signal measuring apparatus according to another exemplary embodiment.

FIG. 8 is a schematic view illustrating a Raman signal measuring apparatus 1300 according to another exemplary embodiment.

The Raman signal measuring apparatus 1300 includes an illumination optical system 130, a detection optical system 230, and a timing controller 300.

The illumination optical system 130 includes a light source 132 and a first shutter 134. If the timing controller 300 transmits a first timing signal TS1, the first shutter 134 may be operated, and light having a predetermined pulse width may be incident on a target object OBJ. If the light source 132 is a pulse laser, the first shutter 134 may be omitted, and the light source 132 may be controlled by the first timing signal TS1.

The detection optical system 230 includes: a beam splitting device 232 configured to divide light LS scattered from the target object OBJ according to the wavelength of the scattered light LS; and an optical detector 236. The beam splitting device 232 may be a prism. The beam splitting device 232 may refract incident light at different angles according to the wavelength of the incident light. For example, a relatively long wavelength may be refracted at a relatively large angle, and a relatively short wavelength may be refracted at a relatively small angle. Therefore, if scattered light LS having various wavelengths is incident on the beam splitting device 232, the beam splitting device 232 may output the scattered light LS in different directions according to the wavelengths of the scattered light LS. The optical detector 236 having a plurality of pixels is positioned such that light divided by the beam splitting device 232 may strike the optical detector 236, and thus the intensity of the light may be detected according to the wavelengths of the light, thereby obtaining a Raman spectrum.

A second shutter 234 may be further disposed between the beam splitting device 232 and the optical detector 236. The second shutter 234 may be closed according to a second timing signal TS2 transmitted from the timing controller 300, so as to terminate the detection of light LS scattered from the target object OBJ.

The position of the second shutter 234 is not limited to the position shown in FIG. 8. For example, the second shutter 234 may be disposed between the beam splitting device 232 and the target object OBJ.

Although it is illustrated that the beam splitting device 232 is a prism, the beam splitting device 232 is not limited to a prism. For example, the beam splitting device 232 may be a grating device configured to split light having various wavelengths by using the property that light is diffracted by a slit at varying angles according to the wavelength of the light.

Figure 9:
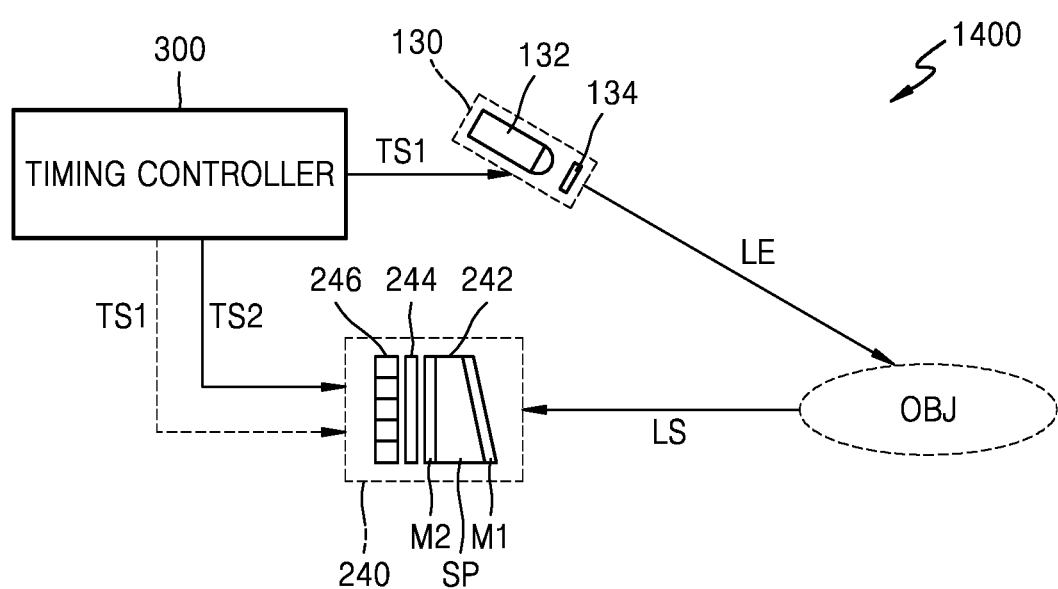
FIG. 9 is a schematic view illustrating a Raman signal measuring apparatus according to another exemplary embodiment.

FIG. 9 is a schematic view illustrating a Raman signal measuring apparatus 1400 according to another exemplary embodiment.

The Raman signal measuring apparatus 1400 includes an illumination optical system 130, a detection optical system 240, and a timing controller 300.

The illumination optical system 130 includes a light source 132 and a first shutter 134. If the timing controller 300 transmits a first timing signal TS1, the first shutter 134 may be operated, and light having a predetermined pulse width may be incident on a target object OBJ. If the light source 132 is a pulse laser, the first shutter 134 may be omitted, and the light source 132 may be controlled by the first timing signal TS1.

The detection optical system 240 may include a linear variable filter 242 as a light splitting element, and the linear variable filter 242 may have different wavelength pass bands according to positions at which light is incident on the linear variable filter 242.

The linear variable filter 242 includes: two reflectors M1 and M2 facing each other; and a spacer SP disposed between the two reflectors M1 and M2 and having a gradually varying thickness. Since different wavelengths are transmitted through the spacer SP according to the thickness of the spacer SP, different light intensities may be detected from the different wavelengths by pixels of an optical detector 246 disposed near the linear variable filter 242, and thus a Raman spectrum may be measured.

A second shutter 244 may be further disposed between the linear variable filter 242 and the optical detector 246. The second shutter 244 may be closed according to a second timing signal TS2 transmitted from the timing controller 300, so as to terminate the detection of light LS scattered from the target object OBJ.

The position of the second shutter 244 is not limited to the position shown in FIG. 9. For example, the second shutter 244 may be disposed between the linear variable filter 242 and the target object OBJ.

Figure 10:
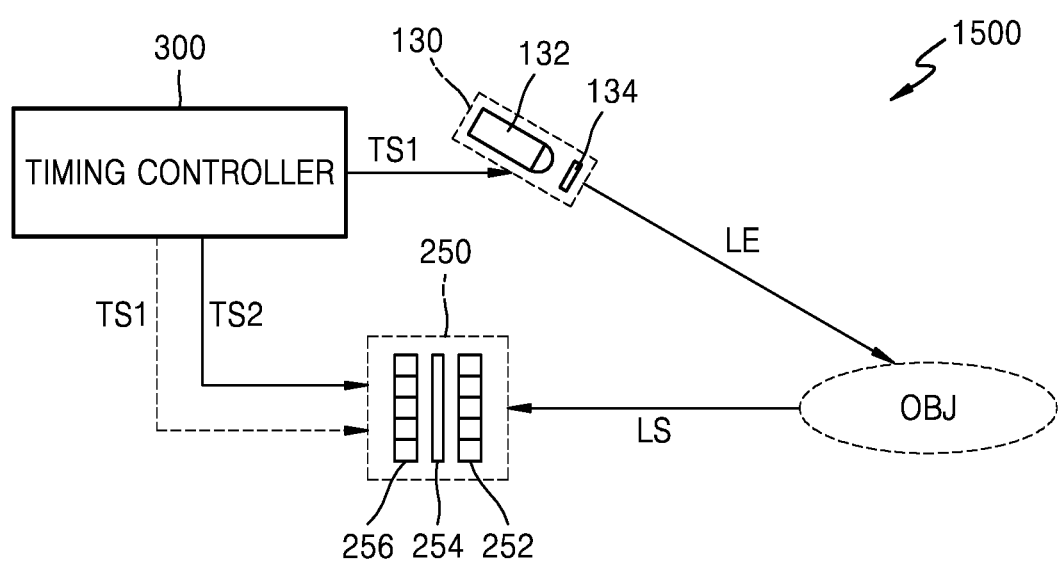
FIG. 10 is a schematic view illustrating a Raman signal measuring apparatus according to another exemplary embodiment.

FIG. 10 is a schematic view illustrating a Raman signal measuring apparatus 1500 according to another exemplary embodiment.

In the previous exemplary embodiments illustrated in FIGS. 8 and 9, the detection optical system 230 or 240 is used to obtain a continuous Raman spectrum. However, the Raman signal measuring apparatus 1500 of the current exemplary embodiment includes a filter array type detection optical system 250 to selectively detect desired Raman peaks.

The Raman signal measuring apparatus 1500 includes an illumination optical system 130, the detection optical system 250, and a timing controller 300.

The illumination optical system 130 includes a light source 132 and a first shutter 134. If the timing controller 300 transmits a first timing signal TS1, the first shutter 134 may be operated, and light having a predetermined pulse width may be incident on a target object OBJ. If the light source 132 is a pulse laser, the first shutter 134 may be omitted, and the light source 132 may be controlled by the first timing signal TS1.

The detection optical system 250 includes: a filter array 252 in which band pass filters having different wavelength pass bands are arranged; and an optical detector 256.

The wavelength pass bands of the band pass filters of the filter array 252 may be determined according to Raman peaks to be measured. Pixels of the optical detector 256 disposed near the filter array 252 may detect different light intensities in different wavelength bands, and thus a Raman spectrum may be measured.

A second shutter 254 may be further disposed between the filter array 252 and the optical detector 256. The second shutter 254 may be closed according to a second timing signal TS2 transmitted from the timing controller 300, so as to terminate the detection of light LS scattered from the target object OBJ.

The position of the second shutter 254 is not limited to the position shown in FIG. 10. For example, the second shutter 254 may be disposed between the filter array 252 and the target object OBJ.

Figure 11:
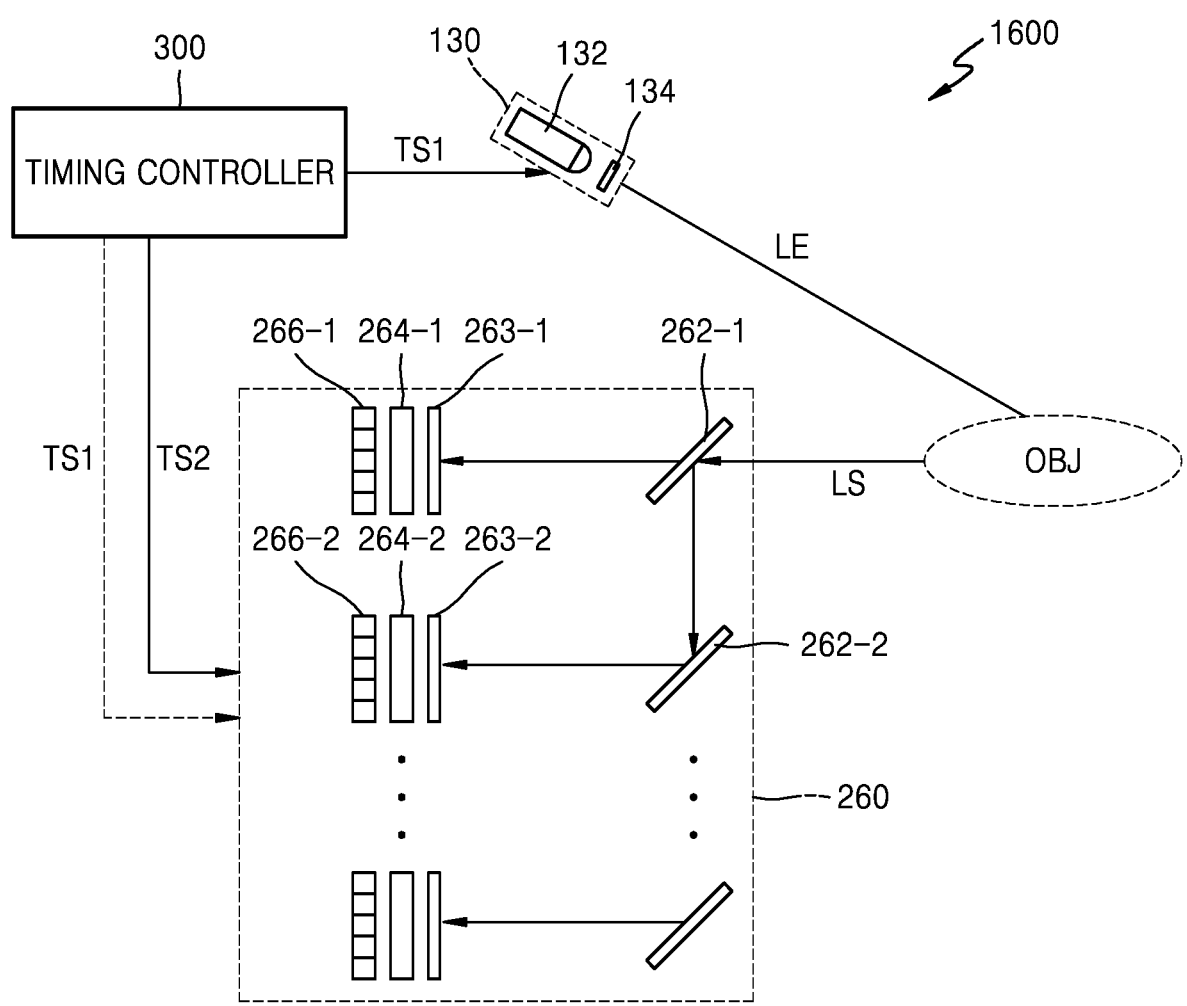
FIG. 11 is a schematic view illustrating a Raman signal measuring apparatus according to another exemplary embodiment.

FIG. 11 is a schematic view illustrating a Raman signal measuring apparatus 1600 according to another exemplary embodiment.

Like the Raman signal measuring apparatus 1500 illustrated in FIG. 10, the Raman signal measuring apparatus 1600 of the current exemplary embodiment includes a detection optical system 260 configured to selectively detect Raman peaks of interest.

The Raman signal measuring apparatus 1600 includes an illumination optical system 130, the detection optical system 260, and a timing controller 300.

The illumination optical system 130 includes a light source 132 and a first shutter 134. If the timing controller 300 transmits a first timing signal TS1, the first shutter 134 may be operated, and light having a predetermined pulse width may be incident on a target object OBJ. If the light source 132 is a pulse laser, the first shutter 134 may be omitted, and the light source 132 may be controlled by the first timing signal TS1.

The detection optical system 260 includes: a plurality of dichroic filters such as a first dichroic filter 262-1 and a second dichroic filter 262-2; and a plurality of optical detectors such as a first optical detector 266-1 and a second optical detector 266-2.

Each of the dichroic filters transmits particular wavelengths of light (i.e., facilitates the propagation of the particular wavelengths of light), but reflects the other wavelengths of the light. For example, the dichroic filters may include: the first dichroic filter 262-1 transmitting light in a first wavelength band and reflecting the light in the other wavelength bands; and the second dichroic filter 262-2 disposed in an optical path of the light reflected by the first dichroic filter 262-1 for transmitting the light in a second wavelength band and reflecting the light in the other wavelength bands.

The number and wavelength pass bands of the dichroic filters may be determined according to Raman peaks of interest.

A plurality of band pass filters having different wavelength pass bands, such as a first band pass filter 263-1 and a second band pass filter 263-2, may be further disposed between the dichroic filters and the optical detectors.

A plurality of second shutters, such as second shutters 264-1 and 264-2, may be further disposed between the band pass filters and the optical detectors. The second shutters 264-1 and 264-2 may be closed according to a second timing signal TS2 transmitted from the timing controller 300, so as to terminate the detection of light LS scattered from the target object OBJ.

The positions of the second shutters 264-1 and 264-2 are not limited to the positions shown in FIG. 11. For example, the second filters 264-1 and 264-2 may be disposed between the dichroic filters 262-1, 262-2 and the band pass filters 263-1, 263-2. Instead of the plurality of second shutters 264-1 and 264-2, only one second shutter may be disposed between the target object OBJ and the first dichroic filter 262-1.

The Raman signal measuring apparatuses 1300, 1400, 1500, and 1600 respectively described above with reference to FIGS. 8, 9, 10, and 11 include the illumination optical systems 130 and the detection optical systems 230, 240, 250, and 260. In addition, the Raman signal measuring apparatuses 1300, 1400, 1500, and 1600 may further include various optical elements configured to direct or guide light from the illumination optical systems 130 to target objects OBJ and direct or guide scattered light LS from the target objects OBJ to the detection optical systems 230, 240, 250, and 260. For example, each of the illumination optical systems 130 may further include an element such as any of an aperture stop, an optical path changer, a collimating lens, a relay lens, and/or an object lens. In addition, each of the detection optical systems 230, 240, 250, and 260 may include an element such as any of an aperture stop, a collimating lens, and/or an object lens.

Figure 12:
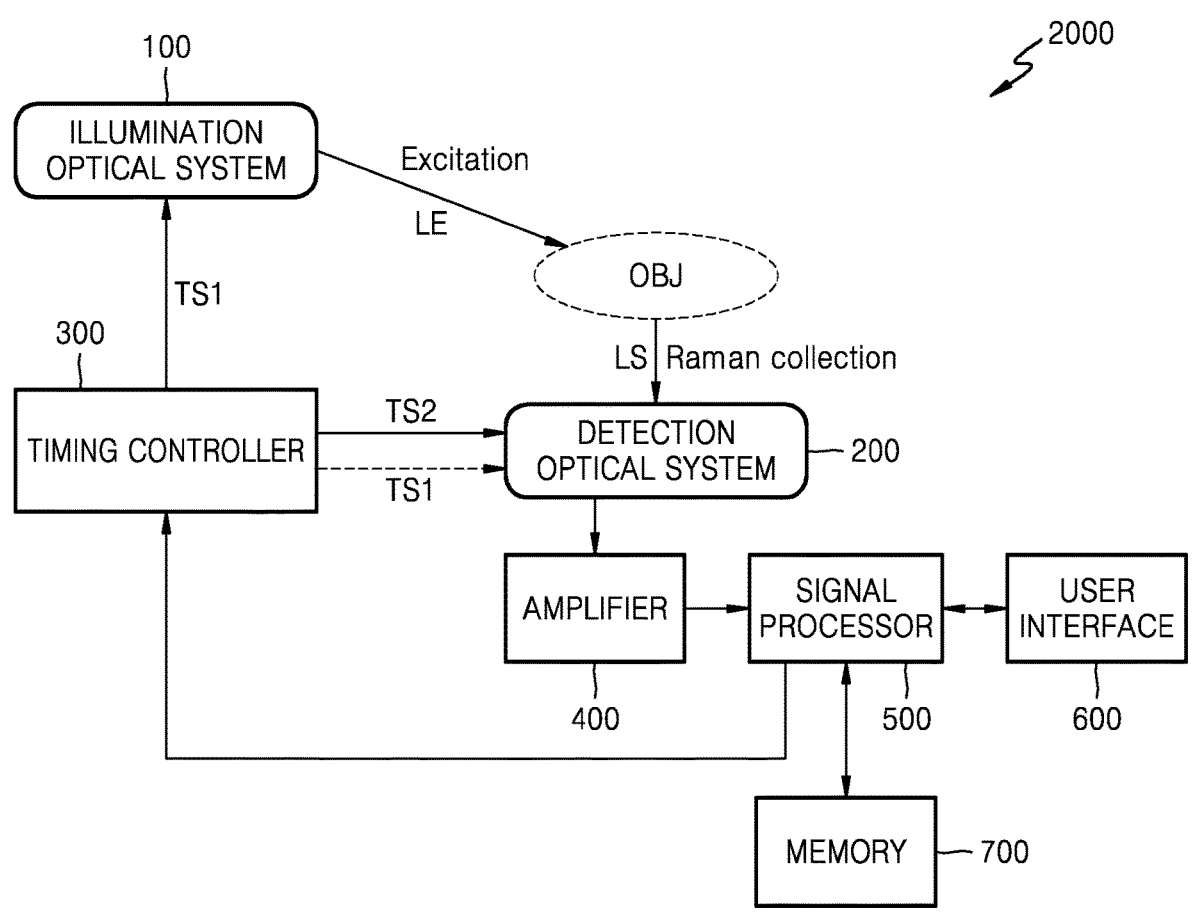
FIG. 12 is a block diagram illustrating a biometric information analyzing apparatus according to an exemplary embodiment.

FIG. 12 is a block diagram illustrating a biometric information analyzing apparatus 2000 according to an exemplary embodiment.

The biometric information analyzing apparatus 2000 may be used for measuring and analyzing biological substances or the composition of living organisms in a non-invasive method.

The biometric information analyzing apparatus 2000 includes: an illumination optical system 100 including a light source configured to emit exciting light to a target object OBJ; a detection optical system 200 including an optical detector configured to detect light LS scattered from the target object OBJ; a timing controller 300 configured to control an operation timing of each of the illumination optical system 100 and the detection optical system 200; and a signal processor 500 configured to analyze properties of the target object OBJ using signals output from the detection optical system 200.

The biometric information analyzing apparatus 2000 may further include: an amplifier 400 configured to amplify signals detected by the detection optical system 200; a user interface 600 configured to provide analysis results of the signal processor 500 to users; and/or a memory 700 that stores programs and data necessary for operations of the signal processor 500.

The biometric information analyzing apparatus 2000 of the current exemplary embodiment uses one of the above-described Raman signal measuring apparatuses 1100, 1200, 1300, 1400, 1500, and 1600. The biometric information analyzing apparatus 2000 may employ the configuration of the illumination optical system 110, 120, or 130 and the configuration of the detection optical system 210, 220, 230, 240, 250, or 260.

The light source of the illumination optical system 100 may rapidly operate before fluorescence is generated from the target object OBJ. The light source may provide pulsed light. The light source may include a continuous wave laser and a chopper, or may include a mode-locking pulse laser, so as provide pulsed light. The pulse width of the pulsed light may be shorter than a time period required until fluorescence is generated from the target object OBJ.

The detection optical system 200 includes a light splitting element and the optical detector. In addition, the detection optical system 200 may further include a shutter, and the shutter may be operated under the control of the timing controller 300 to prevent light LS scattered from the target object OBJ from reaching the optical detector. The optical detector may be a high-speed optical detector having a light detection response time shorter than a time period required until fluorescence is generated from the target object OBJ. For example, the optical detector may have a light detection response time within the range of about 1 nanosecond to about 2 nanoseconds.

In order to detect light emerging from the target object OBJ before the generation of fluorescence, the illumination optical system 100 and the detection optical system 200 may enter a lock-in state under the control of the timing controller 300. The timing controller 300 may include a local oscillator capable of generating waves in a gigahertz (GHz) or higher frequency band, so as to generate a proper timing signal.

The timing controller 300 may generate a timing signal so as to terminate the detection of light by the detection optical system 200 before fluorescence is generated from the target object OBJ in response to exciting light LE emitted from the illumination optical system 100. The timing controller 300 may transmit a first timing signal TS1 to the illumination optical system 100, and the illumination optical system 100 may emit exciting light LE to the target object OBJ according to the first timing signal TS1. At the same time, the timing controller 300 may transmit the first timing signal TS1 to the detection optical system 200. Then, the detection optical system 200 may detect light LS scattered from the target object OBJ according to the first timing signal TS1 received from the timing controller 300. However, this is an example. It is optional whether the timing controller 300 transmits the first timing signal TS1 to the detection optical system 200. When the illumination optical system 100 does not emit exciting light LE to the target object OBJ, since light is not scattered from the target object OBJ, the detection optical system 200 may wait in detection mode, and if exciting light LE is emitted to the target object OBJ according to the first timing signal TS1, the detection optical system 200 may detect light LS scattered from the target object OBJ.

The timing controller 300 may transmit a second timing signal TS2 to the detection optical system 200. After the first timing signal TS1 is transmitted, the second timing signal TS2 is transmitted to the detection optical system 200 before the elapse of a time period $t_{FL}$ required until fluorescence is generated from the target object OBJ in response to exciting light LE. That is, a time difference Δt between the second timing signal TS2 and the first timing signal TS1 is shorter than the time period $t_{FL}$ taken for the target object OBJ to generate fluorescence. The detection of light by the detection optical system 200 may be terminated according to the second timing signal TS2.

The signal processor 500 analyzes properties of the target object OBJ using signals output from the detection optical system 200. For example, the signal processor 500 may analyze substances included in tissue or blood of the target object OBJ and/or the composition of the target object OBJ. The properties of the target object OBJ may be analyzed by a Raman analysis method.

When light of a single wavelength is scattered from the target object OBJ while the light interacts with molecular vibrations of substances of the target object OBJ, the energy state of the light is shifted. The Raman analysis method uses such energy state shifts. Exciting light LE emitted from the illumination optical system 100 to the target object OBJ is scattered from molecular structures of the target object OBJ, and the scattered light LS may have wavelengths shifted from the wavelength of the exciting light LE. The scattered light LS, that is, a biological optical signal, may have various spectrums because the degree of wavelength shift of the scattered light LS is varied according to the molecular state of the target object OBJ. A detected Raman signal includes information about wavelengths shifted from the wavelength of incident light, and such wavelength shifts are energy shifts including information about molecular vibrations of substances such as information about molecular structures, molecular bonds, or functional groups.

Different Raman peaks appear in a Raman spectrum according to the molecular composition of the target object OBJ. For example, substances such as glucose, urea, ceramides, keratin, or collagen may be included in intercellular fluids or blood of the target object OBJ. For example, glucose may exhibit Raman shifts of about 436.4 $cm^{-1}$, about 1065 $cm^{-1}$, about 1126.4 $cm^{-1}$, and about 525.7 $cm^{-1}$ in wavenumber. Collagen may exhibit Raman shifts of about 855 $cm^{-1}$ and about 936 $cm^{-1}$ in wavenumber. Urea may exhibit a Raman shift of about 1000 $cm^{-1}$ in wavenumber.

The signal processor 500 may analyze the distribution amounts of substances from the intensity of spectrum peaks appearing because the wavelength of exciting light LE is Raman-shifted by the substances. For example, if the intensity of spectrum peaks is high at positions indicating that the frequency of incident light is shifted by about 436.4 $cm^{-1}$, about 1065 $cm^{-1}$, about 1126.4 $cm^{-1}$, and about 525.7 $cm^{-1}$ in wavenumber, the distribution amount of glucose may be large. In addition, if the intensity of spectrum peaks is high at positions indicating that the frequency of incident light is shifted by about 855 $cm^{-1}$ and about 936 $cm^{-1}$ in wavenumber, the distribution amount of collagen may be large.

In this manner, the signal processor 500 may analyze the distribution amounts of substances included in the skin of the target object OBJ and may check the health state of the target object OBJ. As described above, since a Raman signal is obtained before fluorescence is generated from the target object OBJ, background fluorescence may not be included in the Raman signal, and thus the accuracy of measurement and diagnosis may be improved.

In addition, the signal processor 500 may generate control signals so as to control the overall operation of the biometric information analyzing apparatus 2000. The signal processor 500 may convert analysis results into image signals so as to display the image signals on a display of the user interface 600. In addition, the signal processor 500 may transmit a control signal to the timing controller 300 in response to a signal input through the user interface 600. The signal processor 500 may include a device such as a microprocessor.

The user interface 600 may be an interface connecting the biometric information analyzing apparatus 2000 to users and/or interfaces of other external devices. The user interface 600 may include an input unit and the display.

Programs necessary for operations of the signal processor 500 may be stored in the memory 700, and input/output data may be stored in the memory 700. In addition, the memory 700 may store a lookup table providing a relationship between spectrum peaks and amounts of substances, and thus the amounts of substances may be determined from the intensity of Raman spectrum peaks by using the lookup table.

The memory 700 may include a recording medium such as a flash memory, a hard disk, a micro multimedia card, a memory card including a secure digital (SD) card or an extreme digital (XD) card, a random access memory (RAM) a static random access memory (SRAM), a read-only memory (ROM), an electrically erasable programmable read-only memory (EEPROM), a programmable read-only memory (PROM), a magnetic memory, a magnetic disk, or an optical disk.

In addition, the biometric information analyzing apparatus 2000 may further include a communication unit (also referred to herein as a "communicator") that includes a transmitter and a receiver or a transceiver. For example, analysis results may be transmitted to an external device through the communication unit. The external device may be a medical device using analyzed biological information, a printer for printing the analysis results, or a display for displaying the analysis results. In addition, the external device may be a smartphone, a cellular phone, a personal digital assistant (PDA), a laptop personal computer (PC), a mobile device, or a mobile computing device. However, the external device is not limited to the listed devices.

As described above, according to the one or more of the above exemplary embodiments, the Raman signal measuring method and apparatus enables the detection of a Raman signal from a target object while minimizing the amount of background fluorescence in the Raman signal. Therefore, additional optical members or processes may not be used or performed to separate Raman peaks from background fluorescence, and the accuracy and repeatability of measurement may be improved.

The biometric information analyzing apparatus is a non-invasive analyzing apparatus using a Raman analysis method. Since Raman signals having fewer errors are obtainable using the biometric information analyzing apparatus, biological data may be more precisely analyzed for accurate diagnosis.

The apparatuses of the exemplary embodiments may include a processor, a memory storing and executing program data, a permanent storage such as a disk drive, a communication port for communication with an external device, a user interface device such as a touch panel, keys or buttons, and the like. Methods embodied as a software module or an algorithm may be stored on a transitory or non-transitory computer-readable recording medium as computer readable codes or program commands executable by the processor. Examples of a non-transitory computer-readable recording medium include magnetic storage media (e.g., ROM, floppy disks, hard disks, etc.), optical recording media (e.g., CD-ROMs, or DVDs), and the like. The computer-readable recording medium can also be distributed over network-coupled computer systems so that the computer readable code is stored and executed in a distributed fashion. The medium can be read by a computer, stored in a memory, and executed by the processor.

The inventive concept of the present disclosure may be embodied as functional blocks and various processing operations. The functional blocks may be implemented with various hardware and/or software configurations executing specific functions. For example, exemplary embodiments of the present disclosure may employ integrated circuit configurations such as a memory, processing, logic, a look-up table and the like capable of executing various functions upon control of microprocessors or other control devices. In a similar manner to that in which the elements of the exemplary embodiments can be executed with software programming or software elements, the exemplary embodiments may be implemented with a scripting language or a programming language such as C, C++, Java, assembler, and the like, including various algorithms implemented by a combination of data structures, processes, routines or other programming configurations. The functional aspects may be implemented by algorithms executed in one or more processors. Also, the exemplary embodiments may employ conversional arts to establish an electronic environment, process signals, and/or process data. Terms such as "mechanism," "element," "means," and "configuration" may be widely used and are not limited to mechanical and physical configurations. Such terms may have the meaning of a series of routines of software in association with a processor or the like.

Specific executions described herein are merely examples and do not limit the scope of the inventive concept in any way. For simplicity of description, other functional aspects of conventional electronic configurations, control systems, software and the systems may be omitted. Furthermore, line connections or connection members between elements depicted in the drawings represent functional connections and/or physical or circuit connections by way of example, and in actual applications, they may be replaced or embodied as various additional functional connection, physical connection or circuit connections.

It should be understood that the Raman signal measuring method and apparatus and the biometric information analyzing apparatus including the Raman signal measuring apparatus described according to exemplary embodiments should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

What is claimed is:

1. A Raman signal measuring method comprising:
   emitting, from an optical illumination system that includes a light source, exciting light toward a target object;
   detecting, by using an optical detection system that includes an optical detector, light scattered from the target object, before fluorescence is generated from the target object by the exciting light;
   controlling, by a timing controller, an operation timing of the optical illumination system and an operation timing of the optical detection system; and transmitting, by the timing controller, a timing signal that corresponds to a termination of the detection of light by the optical detection system before the fluorescence is generated from the target object by the exciting light.

2. The Raman signal measuring method of claim 1, further comprising:
transmitting a first timing signal to the optical illumination system; and
transmitting a second timing signal to the optical detection system,
wherein a transmission time difference between the transmitting of the first timing signal and the transmitting of the second timing signal is shorter than a time period taken for the fluorescence to be generated from the target object by the exciting light.

3. The Raman signal measuring method of claim 2, wherein the emitting of the exciting light is started according to the first timing signal.

4. The Raman signal measuring method of claim 2, wherein the light scattered from the target object is blocked from being incident on the optical detector according to the second timing signal.

5. The Raman signal measuring method of claim 1, wherein the emitting of the exciting light comprises emitting pulsed light.

6. The Raman signal measuring method of claim 5, wherein the pulsed light has a pulse width that is shorter than a time period taken for the fluorescence to be generated from the target object by the exciting light.

7. The Raman signal measuring method of claim 5, wherein the optical detector has a light detection response time that is shorter than a time period taken for the fluorescence to be generated from the target object by the exciting light.

8. A Raman signal measuring apparatus comprising:
an optical illumination system comprising a light source configured to emit exciting light toward a target object;
an optical detection system configured to detect light scattered from the target object, the optical detection system comprising a light splitting element and an optical detector; and
a processor comprising a timing controller configured to control an operation timing of the optical illumination system and an operation timing of the optical detection system,
wherein the timing controller is further configured to transmit a timing signal that corresponds to a termination of the detection of light by the optical detection system before fluorescence is generated from the target object by the exciting light emitted by the light source.

9. The Raman signal measuring apparatus of claim 8, wherein the timing controller is further configured to transmit, to the optical illumination system, a first timing signal that corresponds to allowing the exciting light emitted by the light source to reach the target object.

10. The Raman signal measuring apparatus of claim 9, wherein the optical illumination system is further configured to emit pulsed light toward the target object.

11. The Raman signal measuring apparatus of claim 10, wherein the optical illumination system further comprises a continuous laser and a chopper.

12. The Raman signal measuring apparatus of claim 10, wherein the optical illumination system further comprises a pulse laser.

13. The Raman signal measuring apparatus of claim 10, wherein the pulsed light has a pulse width that shorter than a time difference between a transmission time of the first timing signal and a transmission time of the second timing signal.

14. The Raman signal measuring apparatus of claim 10, wherein the optical detector has a light detection response time that is shorter than a time difference between a transmission time of the first timing signal and a transmission time of the second timing signal.

15. The Raman signal measuring apparatus of claim 9, wherein the light source is further configured to emit the exciting light toward the target object according to the first timing signal.

16. The Raman signal measuring apparatus of claim 9, wherein the optical illumination system further comprises a first shutter configured to open or close an optical path of the light emitted by the light source toward the target object, and
the first shutter is opened according to the first timing signal.

17. The Raman signal measuring apparatus of claim 9, wherein the optical detection system further comprises a second shutter configured to open or close an optical path along which light scattered from the target object propagates toward the optical detector, and
the second shutter is closed according to the second timing signal.

18. The Raman signal measuring apparatus of claim 8, wherein the light splitting element comprises a beam splitting device configured to divide light scattered from the target object according to wavelengths of the scattered light.

19. The Raman signal measuring apparatus of claim 18, wherein the beam splitting device comprises a prism.

20. The Raman signal measuring apparatus of claim 18, wherein the beam splitting device comprises a grating device.

21. The Raman signal measuring apparatus of claim 8, wherein the light splitting element comprises a linear variable filter that has different wavelength pass bands which correspond to respective positions where light is incident upon the linear variable filter.

22. The Raman signal measuring apparatus of claim 8, wherein the light splitting element comprises a plurality of dichroic filters.

23. The Raman signal measuring apparatus of claim 22, wherein the plurality of dichroic filters comprises:
a first dichroic filter configured to facilitate a propagation of light in a first wavelength band and to reflect light outside of the first wavelength band; and
a second dichroic filter arranged in an optical path of the light reflected from the first dichroic filter and configured to facilitate a propagation of light in a second wavelength band and to reflect light outside of the second wavelength band.

24. The Raman signal measuring apparatus of claim 22, wherein each respective one of a plurality of band pass filters that have different wavelength pass bands is arranged between the optical detector and a corresponding one of the plurality of dichroic filters.

25. The Raman signal measuring apparatus of claim 8, wherein the light splitting element comprises a plurality of band pass filters that have different wavelength pass bands.

26. The Raman signal measuring apparatus of claim 8, wherein the optical detection system is further configured to detect Raman-scattered light generated from the target object without detecting fluorescent light generated from the target object.

27. A biometric information analyzing apparatus comprising:

an optical illumination system comprising a light source configured to emit exciting light toward a target object;

an optical detection system comprising an optical detector configured to detect light scattered from the target object;

a processor comprising a timing controller configured to control an operation timing of each of the optical illumination system and the optical detection system; and a signal processor configured to analyze at least one property of the target object by using a signal outputted from the optical detection system, wherein the timing controller is further configured to transmit a timing signal that corresponds to a termination of the detection of light by the optical detection system before fluorescence is generated from the target object by the exciting light emitted by the light source.

* * * * *